United States Patent [19]

Shimizu et al.

[11] 3,939,349
[45] Feb. 17, 1976

[54] METHOD AND DEVICE FOR CLASSIFYING TIRES

[75] Inventors: Masami Shimizu, Kawasaki; Masao Koyama, Hatano, both of Japan

[73] Assignees: Fuji Denki Seizo Kabushiki Kaisha; The Yokohama Rubber Company Ltd., both of Japan

[22] Filed: Dec. 26, 1973

[21] Appl. No.: 428,014

[30] Foreign Application Priority Data

Dec. 27, 1972 Japan.................................. 47-585

[52] U.S. Cl. ............................................ 250/360
[51] Int. Cl. ............................................ G01t 1/16
[58] Field of Search................... 250/358, 359, 360

[56] References Cited
UNITED STATES PATENTS

| | | | |
|---|---|---|---|
| 2,301,251 | 11/1942 | Capen................................ | 250/360 |
| 3,789,226 | 1/1974 | Green et al........................ | 250/360 |

*Primary Examiner*—James W. Lawrence
*Assistant Examiner*—Davis L. Willis
*Attorney, Agent, or Firm*—Robert E. Burns; Emmanuel J. Lobato; Bruce L. Adams

[57] ABSTRACT

During the process of manufacturing tires, vulcanized tires are classified by the utilization of radiations into the white tire having a white rubber compound layer, or a white ribbon, and the black tire having no such white ribbon, while those tires are classified according to the external dimensions such as an inside diameter. More specifically, a radiation source provided on the side of one wallside of a tire emits radiations to the tire at a predetermined angle of inclination, while a radiation detector provided on the side of the other wallside of the tire detects the intensity of radiations which have passed through the tire, whereby the classification of tires is carried out according to the comparison of two outputs which the radiation detector produces at two predetermined relative positions of the tire and the radiation source.

5 Claims, 9 Drawing Figures

METHOD AND DEVICE FOR CLASSIFYING TIRES

BACKGROUND OF THE INVENTION

This invention relates to a method of determining the classification of vehicle tires and especially of vulcanized rubber tires according to the materials used therein and the external dimensions thereof, during the process of manufacturing them, and to a device for practising the method. That is, the method and the device are provided for determining whether or not a tire has a ring-shaped decorative white ribbon in its sidewall and for measuring the inside diameter of a tire.

There are many classifications of vehicle tires. One of the classifications is a so-called "white tire" which has a ring-shaped decorative belt (called as "a white ribbon"), on its sidewall. Tires which have no white ribbons are called as "black tires".

The white ribbon is, in general, provided on a tire by the following method: when the tire is molded, a white rubber compound layer including a white pigment such as titanium oxide or zinc oxide which contains metal having a relatively large atomic number is formed in one sidewall of the tire; and the white rubber compound layer thus formed is covered by a black rubber layer. The tire thus treated is subjected to vulcanization, and then the black rubber layer is removed in order to expose the surface of the white rubber compound layer.

Accordingly, the white tire is the same in appearance as the black tire unless the black rubber layer is removed from the white tire. That is, it is difficult to visually distinguish the white tire from the black tire when the white tire including the white rubber compound layer covered by the black rubber layer has been vulcanized.

In general, in a vulcanization process line, which is one of the process lines for manufacturing tires, vulcanizing prosses for white tires and those for black tires are mixedly provided. Therefore, vulcanized tires to be manufactured as white tires are mixed with vulcanized tires to be manufactured as black tires when they are conveyed out of the valcanization process line. The next process for the vulcanized white tires is different from that for the vulcanized black tires. Accordingly, when those tires have been conveyed out of the vulcanization process line, it is necessary to distinguish the valcanized tires for white tires from those for black tires.

Heretofore, although it is difficult to visually distinguish the valcanized tires for white tires from those for black tires, those two kinds of vulcanized tires have been distinguished from each other by a visual inspection because no method suitable to the distinction has been provided, and the vulcanized tires for white tires thus distinguished from are delivered to the next process for the removal of the black rubber layer.

However, this visual inspector is liable to make a mistake in the classification of the vulcanized tires. That is, the vulcanized tires for manufacturing black tires are often delivered to the process of removing the black rubber layer as a result of which the black tires are seriously damaged.

Furthermore, since the white rubber compound layer is formed in only one of the sidewalls of the white tire, it is necessary to determine which sidewall includes the white rubber compound. This determination has been also conducted by a visual inspection. However, similarly as in the distinction between the white tires and the black tires, it is difficult to visually determine which sidewall includes the white rubber compound layer; therefore, the white tires have often been damaged.

SUMMARY OF THE INVENTION

Accordingly, it is a primary object of this invention to provide a method of classifying tires in which it is possible to distinguish between white tires and black tires and to determine which sidewall of a white tire contains a white ribbon during the process of manufacturing tires, whereby all of the above-described difficulties of conventional methods can be eliminated.

Another object of the invention is to provide a simple device for automatically classifying tires.

The foregoing objects and other objects are achieved by utilizing the property of x-rays or γ-rays that the intensity of the x-rays or γ-rays passing through a substance is decreased, and a degree of this intensity decrease is dependent on the density and thickness of the substance and is greatly dependent on the atomic numbers of the elements constituting the substance.

Hereinafter, the x-rays or γ-rays will be referred to as "radiations". Therefore, the term radiations and "a radiation source" are intended to designate x-rays and a source of x-rays or γ-rays, respectively. In other words, the term radiations herein used do not include α-rays and β-rays and neutron-beams.

According to this invention, the classification of tires is conducted as follows: Radiations emitted from a radiation source provided on the side of one sidewall of a tire are irradiated to the sidewall at a predetermined angle of inclination, and the intensity of radiations which have penetrated through the tire is detected on the side of the other sidewall of the tire, thereby to classify the tire. In this operation, if the relative movement of the tire and the radiation source is effected so that all parts of the sidewall of the tire are irradiated by the radiations, the intensity of radiations which have penetrated through the tire (hereinafter referred to as penetrated radiation intensity when applicable) vary with time, or with the relative movement. According to this variation, the white tires can be distinguished from the black tires, and if the tire is known or identified as a white tire, the side-wall including a white ribbon can be determined.

More specifically, if the radiations are irradiated to the tire at an angle of inclination with respect to the plane of the sidewall of the tire while the relative movement of the tire and the radiation source is effected, two periods of time occur during which the radiations pass through the upper side wall only and through the lower sidewall only. If the tire to be identified or classified is a white tire, one of its sidewalls includes the white rubber compound layer, that is, the white ribbon. That is, one sidewall of the white tire is different in rubber material from the other sidewall. On the other hand, if it is a black tire, both sidewalls thereof are the same in rubber material. Accordingly, in the case of the black tire, the penetrated radiation intensities measured during the two periods of time described above are substantially the same in variation; however, in the case of the white tire, the penetrated radiation intensities measured during the two period of time are different in variation from each other.

This variation can be read by recording with an oscillograph the penetrated radiation intensity detected over the entire tire. Alternately, the variation can be read by a method in which the relative position of the tire and the radiation source is selected so that the radiations pass separately through the sidewalls, the intensity of radiations which have passed one sidewall being compared with that which have passed the other sidewall. In these methods, the relative variation of the penetrated radiation intensity is utilized. Therefore, these methods are advantageous in that the classification of tires is not affected by the variation in intensity of the radiation source or by the variation in dimension of the tire.

A device for practising the method described above, according to this invention, comprises a radiation source provided on the side of one sidewall of a tire, for irradiating radiations to the tire at a predetermined angle of inclination, the tire being relatively moved with respect to the radiation source, radiation detecting means provided on the side of the other sidewall, for detecting the intensity of radiations which have penetrated through the tire to produce an output signal, minimum point detecting means for detecting points where the detection signal has a minumum value, to produce detection signals, period detecting means for detecting from the detection signals of the minimum point detecting means periods of time during which the ratiations penetrate separately through the two sidewalls, maximum value measuring circuits for measuring two maximum values of the output signal of said radiation detecting means, the two maximum values occurring during the periods of time detected by said period detecting means, respectively, and a comparison circuit for comparing the maximum values with each other, thereby to determine the classification of the tire.

In this device, the relative position of the tire and radiation source is detected by processing the detection output signal of the radiation detecting means without the employment of a special position detector. This contributes to the simplification of the device.

Furthermore, the device described above may be modified so that the comparison circuit comprises an operation circuit which carries out the operation for a ratio of one of the maximum values described above to the difference between these two maximum values. In the device thus organized, the variation, due to the variation in intensity of the radiation source and that in dimension of the tire, of the output produced by the comparison circuit is reduced, and accordingly the classification of tires is not affected by such variations.

Furthermore, if means for detecting the relative movement speed of the tire and the radiation source, and means for measuring a period of time between two selectively predetermined minimum points detected by the minimum point detecting means are added to the device described above, the inside diameter and the outside diameter of the tire can be measured, and therefore it is possible to carry out the classification of tires according to the external dimensions thereof.

The nature, utility and principle of this invention will become more apparent when read in conjunction with the accompanying drawings, in which like parts are designated by like reference numerals or characters.

DETAILED DESCRIPTION OF THE INVENTION

A first example of a method of classifying tires according to this invention will be described.

Figure 1A:
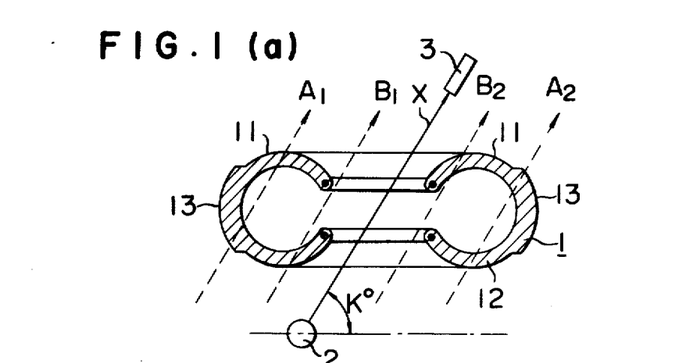
FIG. 1(a) is an explanatory schematic diagram illustrating the positions of lines along which radiations are emitted to a black tire according to a method of this invention.
Figure 1B:
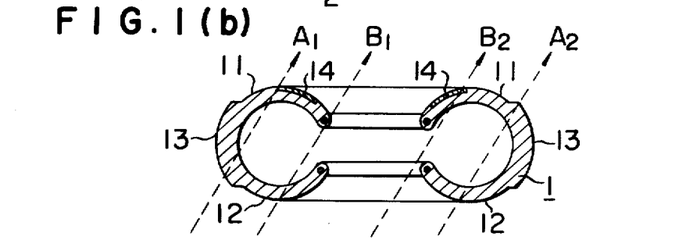
FIG. 1(b) is an explanatory schematic diagram illustrating the positions of lines along which radiations are emitted to a white tire having a white ribbon in its upper sidewall.
Figure 1C:
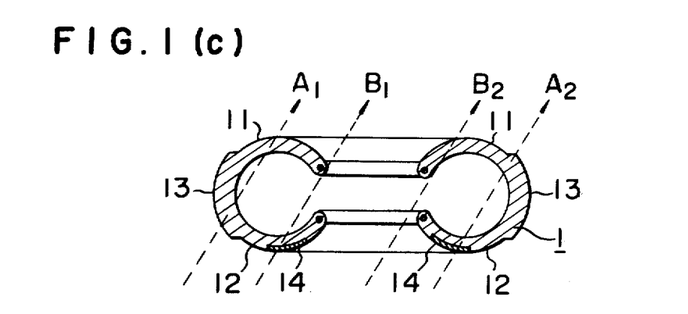
FIG. 1(c) is also an explanatory schematic diagram illustrating the positions of lines along which radiations are emitted to a white tire having a white ribbon in its lower sidewall.

Tires are shown in FIG. 1, each of which comprises two sidewalls 11 and 12 and a tread 13. The tire shown in FIG. 1(a) is a black tire which has no white ribbon made of a white rubber compound in its sidewalls. The tire shown in FIG. 1(b), is a white tire which has the white ribbon in the sidewall 11. The tire shown in FIG. 1(c) is also a white tire which has the white ribbon in the sidewall 12.

Hereinafter, the sidewalls 11 and 12 will be referred to as an upper sidewall 11 and a lower sidewall 12 when applicable, respectively.

According to this invention, the tire 1 is irradiated by radiations $x$, that is, $x$-rays or $\gamma$-rays which are emitted from a radiation source 2 located under the lower side wall 12, the radiations forming a predetermined angle K with the plane of the side wall of the tire 1. The intensity of the radiations $x$ which have penetrated through the tire 1 is detected by a radiation detector 3 provided above the upper sidewall 11.

When the $x$-rays or $\gamma$-rays are applied to the tire, the energy which the rays lose by colliding with heavy elements (whose atomic numbers are great) which are contained in the material of the tire, is greater than that which the rays lose by colliding with light elements (whose atomic numbers are small). Accordingly, the energy which the rays lose by penetrating through the white ribbon made of a white rubber compound layer including a great quantity of metallic elements such as zinc oxide and titanium oxide which is heavier than rubber, is greater than that which the rays lose by penetrating through a black rubber compound layer only, which is a part of the tire 1.

As was briefly described above, the radiation source 2 provided under the lower sidewall 12 of the tire emits the radiations $x$ in a manner such that the radiations $x$ thus emitted penetrate through the tire 1 along dotted lines $A_1$ and $A_2$ and dotted lines $B_1$ and $B_2$ as is shown in FIG. 1; and the radiation detector 3 provided above the upper sidewall 11 detects the intensity of radiations which have penetrated through the tire 1.

In this connection, if the radiation angle of the radiation $x$ is selected to form an angle within the range of from 30° to 70° or from 110° to 150° with the plane of the sidewall 11 or 12, the radiation detector 3 can detect the intensity of radiations which have penetrated through the tire 1 along the lines $A_1$ and $A_2$, that is, the detector 3 can detect the intensity of the radiations which have penetrated through a part of the tread 13 and the upper sidewall 11 and through the lower sidewall 12 and a part of the tread 13; and furthermore the radiation detector 3 can detect the intensity of the radiations $x$ which have penetrated through the tire 1 along the lines $B_1$ and $B_2$, that is, the detector 3 can detect the intensity of the radiations which have penetrated through the lower sidewall 12 only and through the upper sidewall 11 only.

The sidewalls 11 and 12 of the tire shown in FIG. 1(a) include no white ribbon, that is, they are made of the black rubber compound only. Accordingly, the intensity of the radiations which have penetrated through tire (hereinafter referred to as a penetrated radiation intensity, when applicable) along the line $A_1$ is substantially the same as that along the line $A_2$. Similarly, a penetrated radiation intensity along $B_1$ is substantially the same as that along $B_2$. That is, the difference between the penetrated radiation intensity along the line $A_1$ and that along $A_2$ is very small, and the difference between the penetrated radiation intensity along the line $B_1$ and that along $B_2$ is also very small.

The upper sidewall 11 of the tire shown in FIG. 1(b) and the lower sidewall 12 of the tire shown in FIG. 1(c) include the white ribbon 14. That is, in each of the tires shown in FIG. 1(b) and (c), one sidewall is made of the black rubber compound, while the other sidewall is made of the white rubber compound, and therefore two sidewalls are different in radiation penetration characteristic. Accordingly, the penetrated radiation intensities $A_1$ and $A_2$, and $B_1$ and $B_2$ are considerably different from each other.

The penetrated radiation intensities measured by the first example of the method according to this invention are indicated in the following Table 1. In this measurement, plutonium-238 of 30 milli-curies was employed as the radiation source 1, which emitted radiations to the lower sidewall 12 of the tire 1 at a radiation angle of 49°, and a Geiger-Muller counter which was disposed 37 cm. above the radiation source 2 detected and measured the intensity of radiations which penetrated through the tire 1 along the lines $A_1$, $A_2$, $B_1$ and $B_2$.

Table 1

| Kind, Size | Position of measurement | Measured value: cpm (measured 3 times) | | |
|---|---|---|---|---|
| Black tire (6.00-12) | Line $A_1$ | 980 | 1,068 | 1,021 |
|  | Line $A_2$ | 1,013 | 1,053 | 994 |
|  | Line $B_1$ | 14,650 | 14,660 | 14,338 |
| FIG. 1(a) | Line $B_2$ | 14,090 | 14,005 | 13,967 |
| White tire (6.00-12) (with white ribbon on the upper sidewall) | Line $A_1$ | 312 | 271 | 289 |
|  | Line $A_2$ | 668 | 693 | 684 |
|  | Line $B_1$ | 14,417 | 14,376 | 14,405 |
| FIG. 1(b) | Line $B_2$ | 10,763 | 10,600 | 10,622 |
| White tire (6.00-12) (With white ribbon in the lower sidewall) | Line $A_1$ | 690 | 687 | 692 |
|  | Line $A_2$ | 308 | 294 | 276 |
|  | Line $B_1$ | 10,651 | 10,711 | 10,672 |
| FIG. 1(c) | Line $B_2$ | 14,410 | 14,383 | 14,384 |

As is apparent from Table 1, in the measurement of any of the tires, the measured values obtained along the lines $A_1$ and $A_2$ are smaller than those obtained along the lines $B_1$ and $B_2$. This is due to the following reason. That is, the radiations emitted along the lines $A_1$ and $A_2$ go through the tread and one sidewall, while those emitted along the lines $B_1$ and $B_2$ go through one sidewall only. In other words, the thickness of a rubber layer which the former radiations go through is greater that that which the latter radiations go through.

Furthermore, in the measurement of the black tire, the measured values obtained along the lines $A_1$ and $A_2$ are approximately equal to each other, and the measured values obtained along the lines $B_1$ and $B_2$ are also approximately equal to each other. On the other hand, in the measurement of the white tires, the measured values obtained along the lines $A_1$, $A_2$, $B_1$ and $B_2$ are considerably different from one another.

More specifically, in the case of the white tire shown in FIG. 1(b), the radiations emitted along the lines $A_1$ and $B_2$ go through the upper sidewall 11 including the white rubber compound layer 14, while the radiations emitted along the lines $A_2$ and $B_1$ go through the lower sidewall 12 which does not include the white rubber compound layer 14. Accordingly, the measured values obtained along the lines $A_1$ and $B_2$ are smaller than those obtained along the lines $A_2$ and $B_1$, respectively.

In addition, in the case of the white tire shown in FIG. 1(c) which includes the white rubber compound layer 14 is the lower side-wall 12, the radiations emitted along the lines $B_1$ and $A_2$ go through the lower sidewall 12 including the white rubber compound layer 14, while the radiations emitted along the lines $A_1$ and $B_2$ go through the upper sidewall 12 which does not include the white rubber compound layer 14. Accordingly, the measured values obtained along the lines $B_1$ and $A_2$ are smaller than those obtained along the lines $A_1$ and $B_2$, respectively.

It is apparent from Table 1 that the white rubber compound layer reduces the energy of radiations more than the black rubber compound layer. Accordingly, if the measured values obtained along the lines $A_1$ and $A_2$ or the lines $B_1$ and $B_2$ are compared with one another, tires can be classified into the black tire and the white tire according to the differences between the measured values, and furthermore, in the case where the tire has been known or identified as a white tire, it is possible to determine which sidewall includes the white rubber compound layer 14.

This invention has been described in connection with the case where the tire 1 is fixedly held while the combination of the radiation source 2 and the radiation detector 3 are moved to measure the intensity of radiations along the lines $A_1$, $A_2$, $B_1$ and $B_2$. However, the measurement of the pentrated radiation intensity can be achieved by continuously changing the relative position of the tire 1 and the combination of the radiation source 2 and the radiation detector 3. This is a second example of the method according to this invention.

That is, the measurement of the penetrated radiation intensity can be conducted as follows. Similarly as in the previously-described tire classifying method, a radiation source (plutonium-238) 2 is provided under the lower sidewall 12 of a tire 1 in a manner such that the radiation source emits radiations at an angle of 49° with respect to the plane of the sidewall, and a radiation detector 3 is provided above the upper sidewall so as to detect radiations which have penetrated through the tire 1. Furthermore, the radiation source 2 and the radiation detector 3 are fixedly secured, but the tire 1 is moved from right to left as viewed in FIG. 1.

Figures 2A, 2B, 2C:
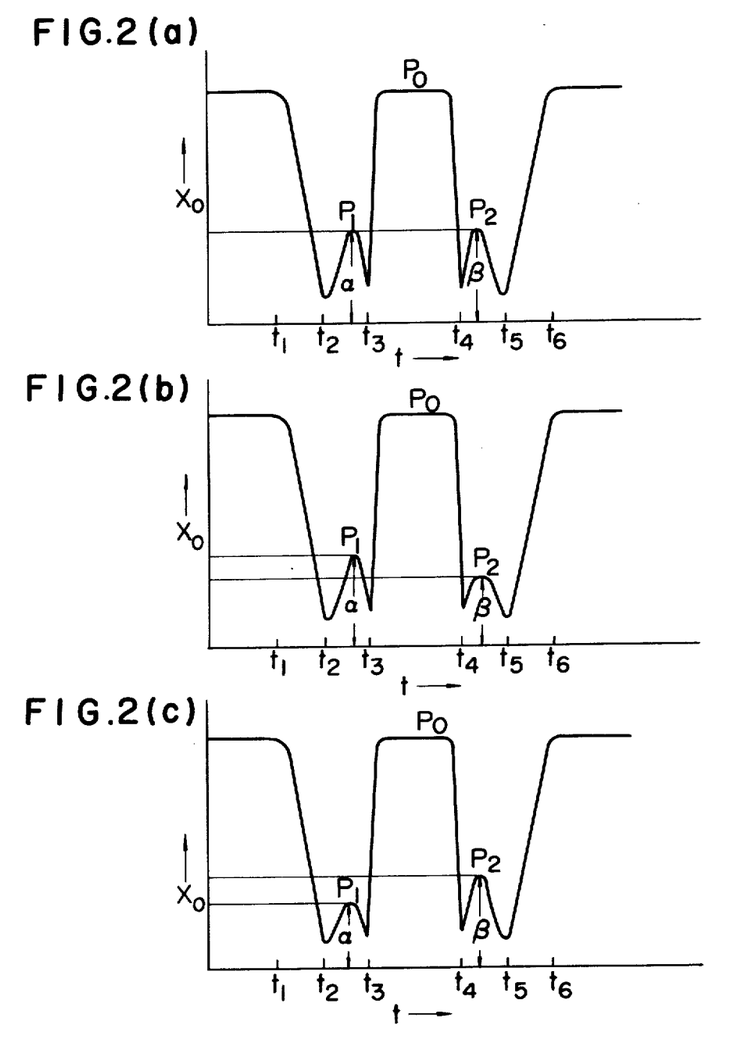
FIG. 2(a) is a graphical representation indicating a waveform of the intensity of radiations which have penetrated through the black tire shown in FIG. 1(a)
FIG. 2(b) is a graphical representation indicating a waveform of the intensity of radiations which have penetrated through the white tire shown in FIG. 1(b)
FIG. 2(c) is also a graphical representation indicating a waveform of the intensity of radiation which have penetrated through the white tire shown in FIG. 1(c)

The intensity of radiations which penetrated through the tire, according to the second example, was continuously recorded by an oscillograph as shown in FIG. 2.

FIGS. 2(a), 2(b) and 2(c) show the variation of penetrated radiation intensity in the case of the black tire shown in FIG. 1(a), that in the case of the white tire shown in FIG. 1(b) which includes the white rubber compound layer in the upper sidewall, and that in the case of the white tire shown in FIG. 1(c) which includes the white rubber compound layer in the lower sidewall, respectively.

In the case of the black tire, as is apparent from FIG. 2(a) a peak $P_1$ occurs at the time instant $t_1$ when the radiations go through the lower sidewall only, and a peak $P_2$ occurs at the time instant $t_2$ when the radiations go through the upper sidewall only. In FIG. 2(a), a relatively flat peak $P_o$ occurs when the radiations go through the central hole of the tire 1. In the cases of the white tires shown in FIG. 1(b) and (c), the time instants when peaks $P_1$ and $P_2$ occur with the white tire shown in FIG. 1(b) are approximately the same as those when peak $P_1$ and $P_2$ occur with the white tire shown in FIG. 1(c).

In the case of the black tire (FIG. 1(a) and FIG. 2(a)), the peaks $P_1$ and $P_2$ are approximately the same in height; in the case of the white tire having the white rubber compound layer in its upper sidewall (FIG. 1(b) and FIG. 2(b)), the height of the peak $P_1$ is taller or greater than that of the peak $P_2$; and in the case of the white tire having the white rubber compound layer in its lower sidewall (FIG. 1(c) and FIG. 2(c)), the height of the peak $P_1$ is smaller than that of the peak $P_2$.

Thus, according to the pattern of the penetrated radiation intensity thus recorded, tires can be classified into the black tire and the white tire, and if a tire is classified or known as a white tire it is possible to determine which sidewall contains the white rubber compound layer.

One example of the tire classifying device, according to this invention, to practise the above-described methods of identifying tires will be described with reference to FIG. 3.

In this tire classifying device, a tire 1 is moved by conveying means (not shown) such as a belt-conveyer from right to left passing between a radiation source 2 and a radiation detecror 3. It is preferable to employ an x-ray generator or a γ-ray generator as the radiation source 2 and to employ an ion chamber as the radiation detector 3, so that the intensity $x_o$ of radiations which have penetrated through the tire 1 can be obtained as an electrical signal A.

The tire classifying device further comprises: a differentiation circuit 31 for effecting the second differential of the output signal A produced by the detector 3; a waveform shaping circuit 32 for shaping only the positive pulses of the differentiation output pulses B produced by the differentiation circuit 31, thereby to produce a synchronous pulses C; a counter circuit 33 for counting the synchronous pulses C; filp-flop circuits $FF_1$ and $FF_2$ which arc set and reset by the outputs I through IV produced by the counter circuit 33, to control the operating periods of maximum value measuring circuits 34 and 35; a comparison circuit 36 for carrying out a substration operation (F − G) in order to compare the output F of the circuit 34 with that G of the circuit 35; and a decision circuit 37 for deciding the magnitude of a comparison output H produced by the comparison circuit 36 thereby to produce a decision output.

In this device, the differentiation circuit 31 is employed for detecting minimum points of the output signal A. The method of detecting this minimum point will be described in detail later. The detection of the minimum points is utilized as a basis to determine the periods of time during which the radiations pass through the upper and the lower sidewall. Since these periods of time are considerably long, it is not always necessary to conduct the detection of the minimum points with accuracy. Accordingly, even if the first differential circuit is employed in place of the second differential circuit 32 in a manner such that its output voltage is detected approximately at a zero point, the minimum points can be practically detected.

The operation of the tire classifying device thus organized will be described with reference to FIGS. 3 and 4.

It is assumed that the white tire 1 including the white rubber compound layer 14 is moved at constant speed in the direction of the arrow by passing through between the radiation source 2 and the radiation detector 3.

Figure 4:
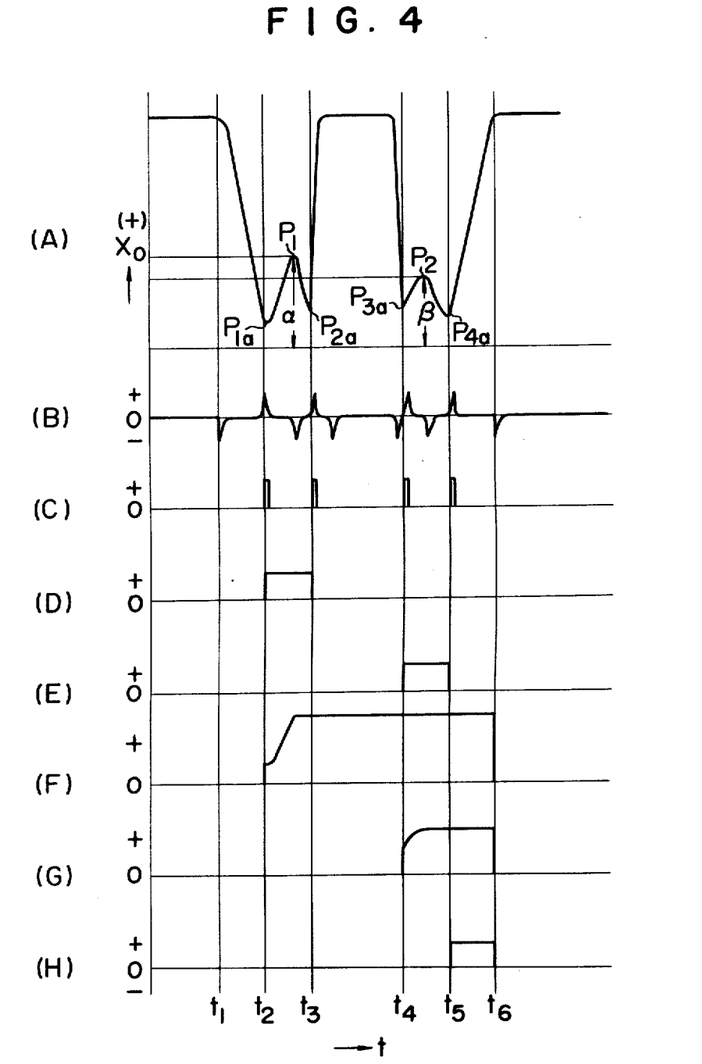
FIG. 4 is also a graphical representation illustrating various signals which are produced by various circuits of the device shown in FIG. 3.

In this case, the detector 3 produces an output signal A whose amplitude varies with time as is shown in (A), FIG. 4. The output signal A indicates the variation of the penetrated radiation intensity and has four minimum points $P_{1a}$, $P_{2a}$, $P_{3a}$ and $P_{4a}$ as is shown in (A), FIG. 4.

When this signal A is subjected to the second differential by the differentiation circuit 31, differentiation pulses B are produced by the circuit 31 as is shown in (B), FIG. 4. These pulses B occur at the time instants $t_1$ through $t_6$ when the signal A changes its amplitude. Of the differentiation pulses B, the positive pulses occur at the time instants when the signal A changes to increase its amplitude, that is, at the time instants corresponding to the minimum points $P_{1a}$, $P_{2a}$, $P_{3a}$ and $P_{4a}$. Accordingly, the rectangular waveform pulses C are produced by the waveform shaping circuit 32 by shaping the positive pulses of the differentiation pulses B in synchronization with the occurrence of the minimum points $P_{1a}$, $P_{2a}$, $P_{3a}$ and $P_{4a}$, respectively.

The counter circuit 33 counts these synchronous pulses C, and whenever it counts a synchronous pulse C, it sequentially applies a count output to its output terminals I through IV. More specifically, when the counter 33 counts one synchronous pulse C, it produces an output I at the output terminal I; when it counts two pulses C, it produces an output II at the terminal II; when it counts three pulses C, it produces an output III at the output terminal III; and so forth.

The flip-flop circuit $FF_1$ is set and reset by the output I and the output II of the counter circuit 33, respectively. As is shown in (D), FIG. 4, the flip-flop circuit $FF_1$ produces an output signal D for the period of time of from the time instant $t_2$ (when the signal A first attains a minimum value) to the time instant $t_3$ (when the signal A next attain a minimum value), thereby to operate the maximum value measuring circuit 34.

The flip-flop circuit $FF_2$ is set and reset by the output III and the output IV, respectively. Similarly as in the operation of the flip-flop circuit $FF_1$, the flip-flop circuit $FF_2$ produces an output signal E for the period of time of from the time instant $t_4$ to the time instant $t_5$ as is shown in (E), FIG. 4 thereby to operate the maximum value measuring circuit 35.

Thus, the maximum value measuring circuit 34 and 35 measure the maximum values of the signal A for the periods of time of from the time instant $t_2$ to the time instant $t_3$ and from the time instant $t_4$ to the time instant $t_5$, and produce output signals F and G, respectively. Accordingly, these output signals F and G are correspondent to the value $\alpha$ of the peak point $P_1$ and the value $\beta$ of the peak point $P_2$, respectively.

The outputs F and G thus produced are applied to the comparison circuit 36, which conducts a subtraction operation (F - G) to compare the output F with the output G. The result H of this subtraction operation is applied to the decision circuit 37. The decision circuit 37 operates to determine if the result of the subtraction operation is H>O or H = O or H<O, and produces a decision output signal J. The signal J thus produced is applied to one of its output terminals BL, WU and WL. When the signal J is applied to the output terminal BL, it means that the tire measured by the tire classifying device is a black tire; when the signal J is applied to the output terminal WU, it means that the tire measured is a white tire having the white rubber compound layer 14 in its upper side-wall; and when the signal J appears at the terminal WL, it means that the tire is a white tire having the white rubber compound layer in its lower sidewall.

Figure 3:
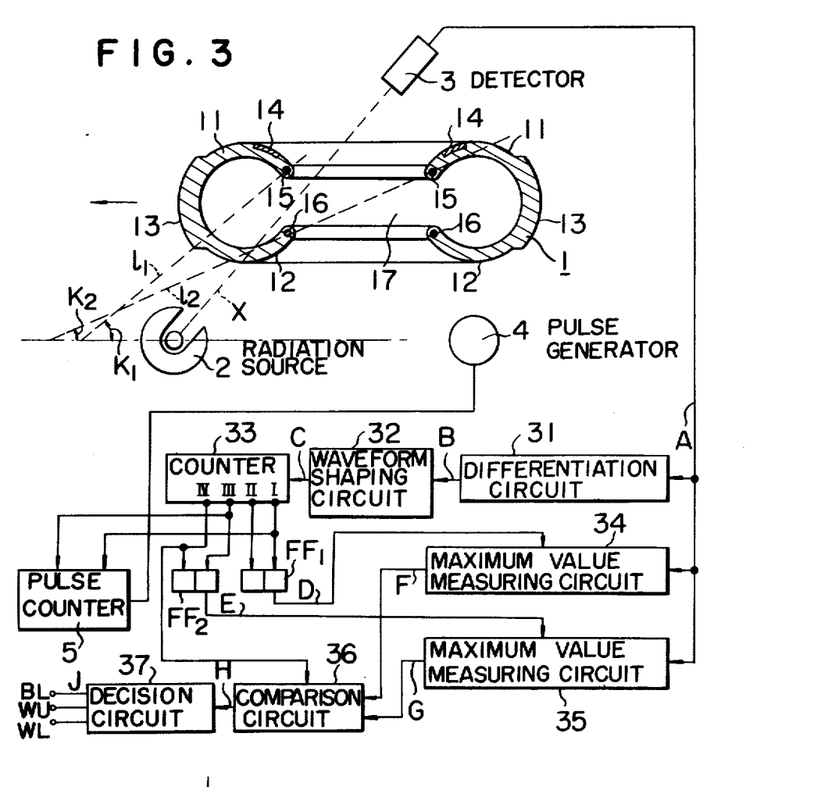
FIG. 3 is a block diagram illustrating a device for classifying tires according to this invention.

In the case when, as is shown in FIG. 3, a white tire having the white rubber compound layer in its upper sidewall is subjected to the measurement, the relationship between the maximum value $\alpha$ occurring between the minimum points $P_{1a}$ and $P_{2a}$ of the signal A (FIG. 4) and the maximum value $\beta$ occurring between the minimum points $P_{3a}$ and $P_{4a}$ is: $\alpha$>B. Therefore, the result of the substraction operation by the comparison circuit 36 is: H>O. The decision circuit 37 discriminates this result (H>O) and applies the decision output signal J to the output terminal WU, as a result of which the tire measured is detected as a white tire having the white rubber compound layer in its upper sidewall.

If the result of the subtraction operation is: H = O, it means that the maximum value $\alpha$ is equal to the maximum value $\beta$. This is the specific feature attained when the black tire is measured. Accordingly, the decision circuit 37 produces the decision output signal J at the output terminal BL. Furthermore, if the result of the subtraction operation is: H<O, the relationship between the maximum values $\alpha$ and $\beta$ is: $\alpha<\beta$. This is the specific feature attained in the measurement of the white tire having the white rubber compound layer in the lower sidewall. Therefore, the decision circuit 37 operates to produce the decision output signal J at the output terminal WL.

In the tire classifying device, the minimum points of the output signal A produced by the detector 3 are detected, and two periods of time during which the radiations go through the lower sidewall 12 only and the lower sidewall 11 only are obtained from the minimum points thus detected, and the maximum value of the signal A is measured in each of the two period of time, thereby to obtain two maximum values $\alpha$ and $\beta$ described above for the classification of tires. Accordingly, in this invention, the provision of a tire position detector is not necessary for the detection of the maximum values $\alpha$ and $\beta$.

In the tire classifying device shown in FIG. 3, the comparison of the maximum values $\alpha$ and $\beta$ is conducted through a subtraction operation. However, in general, the penetrated radiation intensity varies almost exponentially with respect to the thickness of a substance through which the radiation go. Accordingly, it is unavoidable that the output of the comparison circuit 36 greatly varies with the shape and accordingly dimensions of a tire to be classified. In order to reduce the variation of the output of the comparison circuit, the above-described device may be modified so that the comparison circuit obtains a ratio of the difference between the maximum values $\alpha$ and $\beta$ to the maximum value $\alpha$, that is, $(\alpha-\beta)/\alpha$.

If the maximum values $\alpha$ and $\beta$ are compared with each other by the ratio of $(\alpha-\beta)/\alpha$, the variation of the output of the comparison circuit can be reduced due to the following reason.

It is assumed that the thickness of the sidewall of a tire is $x_t$(mm), a ratio of the thickness of a white ribbon to the thickness $x_t$ of the sidewall is $h$ (%), the radiation absorption coefficient of rubber is $\mu r$ (mm)$^{-1}$, the radiation absorption coefficient of the white ribbon is $\mu h$ (mm)$^{-1}$, and the detected intensity of radiations which penetrated through the air is $I_o$. In addition, if the white ribbon is on the $\alpha$ side, the maximum values $\alpha$ and $\beta$ can be represented by the following equations (1) and (2), respectively:

$$\alpha = I_o \exp\{-\mu r\ (1-h)xt - \mu h h xt\} \quad (1)$$
$$\beta = I_o \exp\{-\mu r xt\} \quad (2)$$

Therefore, from equations (1) and (2):
$$(\alpha-\beta) = I_o \exp\{-\mu r xt\} \times [\exp\{-(\mu h - \mu r)hxt\} - 1] \quad (3)$$

$$\left(\frac{\alpha-\beta}{\alpha}\right) = 1 - \exp\{(\mu h-\mu r)\ hxt\} \quad (4)$$

As is apparent from the comparison of these two equations (3) and (4), since equation (4) does not include the term $I_o \exp\{-\mu r\ xt)\}$, the variation of the comparison circuit output owing to the variation of the thickness $xt$ of the tire, or the variation of the dimensions of the tire, can be reduced as much as the term is omitted in equation (4).

According to another aspect of this invention, the inner circumferential edge of the sidewalls of the tire can be detected, because in the tire classifying device shown in FIG. 3, the first and the second synchronous pulse C are produced by the waveform shaping circuit 32 respectively when the radiations $x$ go through the left end of the inner circumference of the upper sidewall and that of the lower sidewall, while the third and the fourth synchronous pulse C are produced when the radiations $x$ go through the right end of the inner circumference of the upper sidewall and that of the lower sidewall.

More specifically, if a speed pulse generator 4 for generating pulses in proportion to a tire moving speed, and a pulse counter circuit 5 for counting the pulses produced by the generator 4 are added to the device shown in FIG. 3 in which a tire 1 is continuously moved as described before while its position is adjusted so that the radiations emitted from the radiation source go through the center line of the tire 1, and if the counting operation of the counter circuit 5 is started by the first signal C or the second signal C described above and is suspended by the third signal C or the fourth signal C; the counter circuit 5 counts the output pulses produced by the speed pulse generator 4 for the period of time of from the time instant when the radiations go through the left end of the inner circumference of the upper wallside or the lower wallside to the time instant when the radiations go through the right end of the same. Accordingly, the inside diameter of the tire 1 can be detected from the count output of the counter circuit 5. Thus, the tire identifying device thus organized can not only identify the black tire and the white tire but also classify the tires by the inside diameter thus measured.

It should be noted that, in the device described above, the radiation angle K of the radiations $x$ is so selected that intensity of the radiations which have penetrated through the tire is varied to four minimum values. Furthermore, the radiation source 2 and the radiation detector 3 are fixedly secured so that the radiation angle K is a certain angle within the range of from the angle of inclination $K_1$ (about 45°) of the line $l_1$ formed by connecting the lower edge of the tread 13 to a steel ring, or a bead wire 15, provided in the circumferential portion of the upper sidewall 11 to the angle of inclination $K_2$ (about 30°) of the line $l_2$ formed by connecting a steel wire 16 provided in the inner circumferential portion of the lower sidewall 12 through the center of the tire 1 to the steel wire 15 in the upper sidewall 11.

Figure 5:
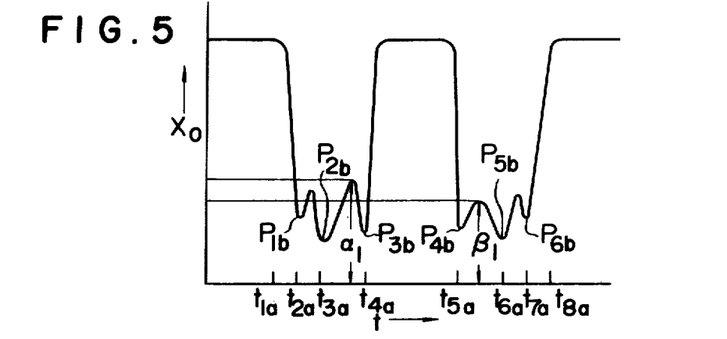
FIG. 5 is also a graphical representation illustrating another waveform obtained by plotting the intensity of radiations which have passed through a white tire at an angle of inclination different from that in the case of FIG. 1.

In addition, the radiation angle K may be selected as 90°> K > $K_1$. In this case, the radiations can simultaneously go through two sidewalls 11 and 12 for two periods of time, that is, a period of time of from the time instant when the radiations go through the tread 13 (on the left side as viewed in FIG. 3) of the tire to the time instant when the radiations go through the steel ring 13 (on the left side as viewed in FIG. 3) of the upper side-wall, and a period of time of from the time instant when the radiations go through the steel ring 16 (on the right side in FIG. 3) of the lower sidewall 12 to the time instant when the radiations go through the tread (on the right side in FIG. 3) of the tire 1. Accordingly, in each of these two periods of time, the penetrated radiation intensity temporarily increases, that is, the output signal A of the radiation detector 3 shows six minimum points $P_{1b}$, $P_{2b}$, $P_{3b}$, $P_{4b}$, $P_{5b}$ and $P_{6b}$ as is illustrated in FIG. 5.

In this variation of the penetrated radiation intensity $x_o$, the maximum value $\alpha_1$ between the second minimum point $P_{2b}$ and the third one $P_{3b}$ represents the intensity of the radiations measured when they go through the lower sidewall 12 only, while the maximum value $\beta_1$ between the fourth minimum point $P_{4b}$ and the fifth one $P_{5b}$ represents the intensity of the radiations measured when they go through the upper sidewall 11 only.

Accordingly, in the measurement of the black tire, the maximum value $\alpha_1$ and $\beta_1$ are equal to each other; in the measurement of the white tire having the white ribbon in its upper sidewall 11, the maximum value $\alpha_1$ is greater than the maximum value $\beta_1$; and in the measurement of the white tire having the white ribbon in its lower sidewall 12, the maximum value $\alpha_1$ is smaller than the maximum value $\beta_2$.

In other words, the maximum value of the penetrated radiation intensity during the period of time of from the time instant $t_{3a}$ when the minimum point $P_{2b}$ occurs to the time instant $t_{4a}$ when the minimum point $P_{3b}$ occurs and that during the period of time of from the time instant $t_{5a}$ when the minimum point $P_{4b}$ occurs to the time instant $t_{6a}$ when the minimum point $P_{5b}$ occurs are measured. By comparing these maximum values thus measured with each other, the black tire and the white tire can be distinguished from each other.

For the measurement and comparison of the maximum values of the penetrated radiation intensity, the device shown in FIG. 3 can be employed, if the connection of the counter 33 to the flip-flops $FF_1$ and $FF_2$ is changed as follows: As was described before, the output terminals I and II of the counter 33 have been connected to the set and reset terminals of the flip-flop $FF_1$, while the output terminals III and IV of the same have been connected to the set and reset terminals of the flip-flop $FF_2$. In addition to these output terminals, a fifth output terminal V is provided in the counter 33 so that when the counter 33 counts five pulses, it produces a count output at the output terminal V. Furthermore, the connection of these output terminals is changed in such a manner that the output terminals II and III are connected to the set and reset input terminals of the flip-flop $FF_1$, while the output terminals IV and V are connected to the set and reset input terminals of the flip-flop $FF_2$. As a result, the first maximum value measuring circuit 34 can measure the maximum value $\alpha_1$ of the penetrated radiation intensity during the period of time of from the time instant $t_{3a}$ to the time instant $t_{4a}$, while the second maximum value measuring circuit 35 can measure the maximum value $\beta_1$ of the penetrated radiation intensity during the period of time of from the time instant $t_{5a}$ to the time instant $t_{6a}$.

The maximum values $\alpha_1$ and $\beta_1$ are compared with each other by the comparison circuit 36. In this operation, similarly as in the comparison described before, the penetrated radiation intensity measured when the radiations go through the upper sidewall only is compared with that obtained when the radiations go through the lower sidewall only. Accordingly, in the case where it is necessary to determine the classification of tires, the tires can be classified into the black tires and the white tires by the device thus organized, and in the case where the tire is known as a white tire, it is possible to determine which sidewall includes the white ribbon.

Even if the radiation angle K is selected greater than the radiation angle $K_1$, no trouble will be caused in the classification of tires. However, as the radiation angle K approaches 90°, the period of time during which the radiations penetrates through the upper sidewall only or the lower sidewall only becomes short. Therefore, it is not preferable that the radiation angle K is greater than a certain angle. That is, there is an angular range allowable for the radiation angle K. According to the experiments on this angular range, it has been found that, when the tire is moved horizontally, the radiation angle within the angular range of from 30° to 75° is best for the classification of tires with the tire classifying device according to the invention.

As is apparent from the above description, in this invention, tires are irradiated by radiations and the intensity of the radiations which have penetrated through the tires is measured for the classification of tires according to the materials and dimentions thereof. This classification is carried out by comparing the intensity of the radiations which have penetrated through the upper sidewall with that of the radiations which have penetrated through the lower sidewall, instead of comparing the radiation intensity with a standard reference value. Accordingly, the variation of the penetrated radiation intensity due to the variations in radiation intensity of the radiation source and in dimension of the tire does not directly affect the accuracy in the classification of tires. Accordingly, tires can be accurately classified or identified.

Furthermore, according to this invention, the penetrated radiation intensity can be measured when the radiations go through the upper sidewall only or the lower sidewall only, without the detection of the position of a tire. Therefore, the provision of a device for detecting the positions of a tire is not necessary for the tire classifying device. This contributes to the simplification of the tire classifying device.

Furthermore, according to this invention, if the speed pulse generator for detecting the moving speed of a tire is added to the device, not only the classification of tires according to the material used therein (classification of tires into the white tires and the black tires) but also the classification of tires according to the external dimensions (classification of tires according to the inside diameters thereof) can be achieved.

We claim:

1. A method of classifying a tire which comprises, (a) emitting x-rays and γ-rays from a radiation source on the side of a first sidewall of said tire and irradiated on said tire sidewall at a predetermined angle of inclination relative to the plane of the tire; (b) detecting the intensity of said x-rays or γ-rays which have penetrated through said tire on the side of a second sidewall of said tire, and (c) comparing with each other the values of intensity of said x-rays or γ-rays which have penetrated separately through said first sidewall and said second sidewall thereby to determine whether said tire is a tire with a white ribbon or said tire is a tire without a white ribbon in a sidewall thereof.

2. A method as claimed in claim 1 in which said radiation source and said tire are relatively moved.

3. A device for classifying a tire which comprises: (a) a radiation source for irradiating x-rays or γ-rays on a first sidewall of a tire at a predetermined angle of inclination relative to the plane of the tire; (b) means for moving said tire relatively to said radiation source; (c) radiation detecting means provided to receive said rays penetrating a second sidewall of said tire, for detecting the intensity of x-rays or γ-rays which have penetrated through said tire and having means for producing an output signal; (d) minimum point detecting means for detecting where said output signal of said radiation detecting means shows minimum values, to produce detection signals; (e) period detecting means for detecting from said detection signals of the minimum point detecting means periods of time during which said x-rays or γ-rays separately penetrate through said first sidewall and said second sidewall; (f) maximum value measuring circuits for measuring two maximum values of said output signal of said radiation detecting means, said two maximum values occuring during said periods of time detected by said period detecting means, respectively; and (g) a comparison circuit for comparing said maximum values with each other, thereby to determine whether said tire is a tire with a white ribbon on a sidewall therefore or is a tire without a white ribbon.

4. A device as claimed in claim 3 in which comparison circuit comprises an operation circuit which carries out the operation for a ratio of one of said two maximum values to the difference between said two maximum values.

5. A device as claimed in claim 3 which further comprises means for measuring the inside diameter of said tire from a period of time between time instants when two selected detection outputs of said minimum point detecting means are produced.

* * * * *